(12) United States Patent
Morita et al.

(10) Patent No.: US 8,558,037 B2
(45) Date of Patent: Oct. 15, 2013

(54) METHOD OF PRODUCING BUTANOL

(75) Inventors: Izumi Morita, Kamakura (JP); Masateru Ito, Kamakura (JP); Hideki Sawai, Kamakura (JP); Shinichi Minegishi, Urayasu (JP); Katsushige Yamada, Kamakura (JP); Kenji Kawamura, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 202 days.

(21) Appl. No.: 13/076,052

(22) Filed: Mar. 30, 2011

(65) Prior Publication Data

US 2012/0253086 A1  Oct. 4, 2012

(51) Int. Cl.
*C07C 29/74* (2006.01)

(52) U.S. Cl.
USPC .......................................... 568/913; 568/918

(58) Field of Classification Search
USPC .................................................. 568/913, 918
See application file for complete search history.

(56) References Cited

U.S. PATENT DOCUMENTS

| 2005/0069997 A1 | 3/2005 | Adkesson et al. |
| 2006/0065600 A1 | 3/2006 | Sunkara et al. |
| 2007/0193960 A1 | 8/2007 | Frank et al. |

FOREIGN PATENT DOCUMENTS

| JP | 57-136905 | 8/1982 |
| JP | 62-201606 | 9/1987 |
| JP | 2003-135090 | 5/2003 |

OTHER PUBLICATIONS

Bhanushali et al., Journal of Membrane Science 189, (2001), pp. 1-21.*

* cited by examiner

*Primary Examiner* — Elvis O Price
(74) *Attorney, Agent, or Firm* — Birch, Stewart, Kolasch & Birch, LLP

(57) ABSTRACT

A method of producing butanol, which has a step of removing impurities contained in a butanol-containing solution, is provided. In the method, a butanol-containing solution is filtered through a nanofiltration membrane. Then the butanol-containing solution is collected from the permeate flow of the nanofiltration membrane.

7 Claims, 1 Drawing Sheet

METHOD OF PRODUCING BUTANOL

BACKGROUND OF THE INVENTION

1. Field of the Invention

The present invention relates to a method of producing butanol by separating butanol from a butanol-containing solution. More particularly, the present invention relates to a method for producing butanol, which method comprises a step of removing inorganic salts, sugars, proteins, catalytic components and/or the like remaining in a butanol-containing solution with a nanofiltration membrane.

2. Description of the Related Art

Butanol is a compound which is industrially very important as a raw material of chemicals and pharmaceutical agents, as a solvent, and as a fuel material. It is well known that butanol can be industrially synthesized from acetaldehyde by the Wacker process, or from propylene, carbon monoxide and water by the Reppe process, and it also has long been known that these can be produced by acetone-butanol fermentation. Production of butanol by acetone-butanol fermentation have problems in that the cost of the substrate to be used as the nutrient source for microorganisms and the cost of purification of the product are high, so that production of butanol has become dependent on chemical synthesis. However, because of the recent decrease in the crude oil resource and substantial rise in its price, production methods of butanol using biomass have been expected to be useful as alternatives to chemical synthesis, and therefore reduction of the production cost in acetone-butanol fermentation is demanded.

In general, as the method for purifying butanol, solvent extraction or distillation is employed. In solvent extraction, in cases where the desired product is a lower alcohol, which is highly soluble in water, distribution of the lower alcohol into the organic phase is difficult, so that use of a special extraction solvent or multistep extraction may be required, which leads to increase in the cost (Patent Document 1). Further, in purification by distillation, since the concentration of butanol in the fermentation broth is low, water, whose boiling point is lower than that of butanol, needs to be distilled off in a large amount, so that a method that enables efficient concentration of butanol is demanded. As a solution to solve the problem, a method for concentrating a fermentation alcohol using a separation membrane has been devised. In Patent Document 2, a method for concentrating an alcohol by the pervaporation separation method using a silicone rubber membrane is disclosed. However, this method is the so called batch filtration concentration wherein purified fermentation broth is recovered from a fermenter and then treated in a pervaporation apparatus under specific conditions, which is not rational in view of device configuration.

Examples of the continuous method for alcohol concentration as an alternative to the batch process include the method using a silicalite membrane coated with silicone rubber, which is disclosed in Patent Document 3. In cases where the operation of concentration is carried out by introducing a silicalite membrane into a fermenter, fouling occurs with time due to organic acids such as succinic acid and malic acid produced as by-products. By coating the surface of the silicalite membrane with the silicone rubber to make the membrane surface hydrophobic, this fouling is suppressed. However, since fouling substances accumulate with time also on the surface of the silicone rubber, the performance of the separation membrane may decrease with time.

Further, in case where an alcohol is distilled from a fermentation broth, sugars, amino acids, side metabolites such as organic acids, and the like remaining in the fermentation broth are heated to yield by-products, which are then contaminated in the distillate fraction as impurities, which is problematic. Therefore, purification of the fermentation broth is also an important problem. As methods for purifying an alcohol, a method for purifying 1,3-propanediol wherein distillation is carried out in combination with microfiltration, ultrafiltration, nanofiltration or ion exchange (Patent Document 4); and a method for separating diol using a reverse osmosis membrane or a nanofiltration membrane (Patent Document 5) are disclosed. However, these prior arts do not disclose the effect of difference in the material of the nanofiltration membrane on the permeation selectivity and on purification of butanol.

PRIOR ART REFERENCES

Patent Documents

Patent Document 1 US 2007/193960 A
Patent Document 2 JP 57-136905 A
Patent Document 3 JP 2003-135090 A
Patent Document 4 US 2005/069997 A
Patent Document 5 US 2006/065600 A

SUMMARY OF THE INVENTION

In view of the above-mentioned purpose, that is, purification of butanol, the present invention aims to provide a method by which butanol can be separated and collected at higher purity and at lower cost than by the conventional methods.

The present inventors intensively studied to solve the above problems and discovered that high-purity butanol can be obtained by filtering a butanol-containing solution through a nanofiltration membrane having a functional layer containing a polyamide, and that the cost of distillation can be effectively reduced by this process, thereby completing the present invention.

That is, the present invention provides the following (1) to (7):

(1) A method of producing butanol, the method comprising the steps of: filtering a butanol-containing solution through a nanofiltration membrane; and collecting butanol-containing solution from the permeate flow of the nanofiltration membrane.

(2) The method according to (1), wherein the butanol-containing solution is a fermentation broth obtained by microbial fermentation.

(3) The method according to (1), wherein the nanofiltration membrane has a functional layer comprising a polyamide.

(4) The method according to (3), wherein the polyamide comprises a cross-linked piperazine polyamide as a major component, and a constituting component represented by Formula [I]:

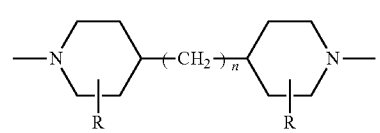

[I]

wherein R represents —H or —CH$_3$, and n represents an integer of 0 to 3.

(5) The method according to (1), further comprising the step of filtering the collected butanol-containing solution through a reverse osmosis membrane to increase the butanol concentration.
(6) The method according to (1), further comprising the step of distilling the collected butanol-containing solution under a pressure of not less than 1 Pa and not more than atmospheric pressure, at 25° C. to 200° C.
(7) The method according to (5), further comprising the step of distilling the butanol-containing solution after concentration through the reverse osmosis membrane under a pressure of not less than 1 Pa and not more than atmospheric pressure, at 25° C. to 200° C.

By the present invention, metal catalysts, inorganic salts and/or sugars existing in a butanol-containing chemically synthesized reaction solution or fermentation broth can be removed by a simple process, and therefore the distillation efficiency can be increased and the cost can be reduced, so that highly pure butanol can be produced at low cost.

DESCRIPTION OF SYMBOLS IN DRAWINGS

Figure 1:
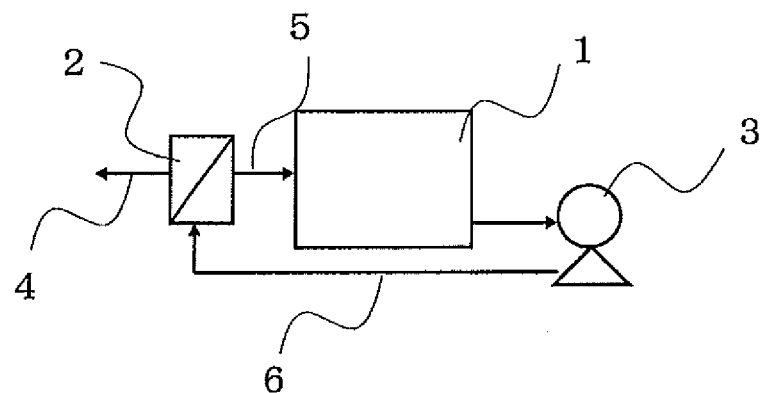
FIG. 1 is a schematic view showing an embodiment of the separation apparatus used in the present invention having a nanofiltration membrane and a reverse osmosis membrane.

1 Feed tank
2 Cell equipped with nanofiltration membrane or reverse osmosis membrane
3 High-pressure pump
4 Permeate flow which has pass through membrane
5 Retentate flow which has been concentrated with membrane
6 Feed flow sent by high-pressure pump 7 Nanofiltration membrane or reverse osmosis membrane
8 Supporting plate

BEST MODE FOR CARRYING OUT THE INVENTION

The present invention will now be described more concretely.

The method of the present invention for producing butanol is a method for producing butanol by separating butanol from a butanol-containing solution, and relates to a method for producing butanol, comprising a step of allowing the butanol-containing solution to pass through a nanofiltration membrane to remove metal catalysts, inorganic salts, sugars and/or the like.

In the present invention, butanol means a collective name of compounds having a hydroxyl group and four carbon atoms, and examples thereof include n-butanol, isobutanol, 2-butanol and 2-methyl-2-propanol. In the present invention, a butanol may comprise a single type of butanol or may be a mixture of plural types of butanols.

The method used in the present invention for producing a butanol-containing solution is not restricted as long as it is known to those skilled in the art, and examples of the method include a method wherein the solution is prepared by the Wacker process from acetaldehyde and a method wherein the solution is prepared by Reppe process from propylene, carbon monoxide and water, as mentioned above, in cases where a chemical synthesis method is used. In terms of fermentation culture, the solution is produced by anaerobic culture of *Clostridium butylicum*. A preferred method for the butanol-containing solution used in the present invention is the method by fermentation culture of a microorganism, and, in this case, the fermentation broth itself containing butanol can be used as the butanol-containing solution to be applied to the nanofiltration membrane.

The nanofiltration membrane used in the present invention is also called NF membrane, and generally defined as a "membrane that allows permeation of monovalent ions but blocks divalent ions". The membrane is considered to have voids of as small as several nanometers, and mainly used for rejection microparticles, molecules, ions, salts and/or the like in water.

By filtering the butanol-containing solution through the nanofiltration membrane, impurities (substances other than butanol) are removed at the feed flow of the nanofiltration membrane and the butanol-containing solution is collected from the permeate flow of the nanofiltration membrane.

Examples of known materials of nanofiltration membranes generally include polymer materials such as cellulose acetate polymers; polyamides; polyesters; polyimides; vinyl polymers including polyvinyl alcohols; and polysulfones, which can be used in the present invention. Among these, a nanofiltration membrane having a polyamide in its functional layer is preferably used in the present invention since high purification efficiency can be attained therewith. Other plural membrane materials may also be contained in the membrane as long as the functional layer contains a polyamide. In terms of the membrane structure, either an asymmetric membrane wherein at least one side of the membrane has a dense layer, which membrane has micropores having a diameter that gradually increases from the dense layer to the inside of the membrane or to the other side of the membrane, or a composite membrane having on the dense layer of an asymmetric membrane a very thin functional layer formed by another material can be used. Examples of the composite membrane which may be used include the composite membrane described in JP 62-201606 A, wherein a nanofiltration membrane having a polyamide functional layer was placed on a support membrane made of a polysulfone membrane material.

The nanofiltration membrane having a polyamide functional layer preferably used in the present invention is preferably a composite membrane having a high pressure resistance, a high permeability and a high solute rejection performance. Further, in order to allow maintenance of durability against the operation pressure, a high permeability and a high rejection performance, the membrane preferably has a polyamide functional layer which is retained by a support made of a porous membrane and/or a non-woven fabric. In a nanofiltration membrane having a polyamide functional layer, preferred examples of the carboxylic component, expressed in terms of monomers, constituting the polyamide include aromatic carboxylic acids such as trimesic acid, benzophenone tetracarboxylic acid, trimellitic acid, pyromellitic acid, isophthalic acid, terephthalic acid, naphthalenedicarboxylic acid, diphenylcarboxylic acid and pyridinecarboxylic acid, and, in view of solubility to the film-forming solvent, trimesic acid, isophthalic acid or terephthalic acid, or a mixture thereof is more preferred.

Preferred examples of the amine component, expressed in terms of monomers, constituting the polyamide include primary diamines having an aromatic ring(s), such as m-phenylenediamine, p-phenylenediamine, benzidine, methylenebisdianiline, 4,4'-diaminobiphenyl ether, dianisidine, 3,3',4-triaminobiphenyl ether, 3,3',4,4'-tetraaminobiphenyl ether, 3,3'-dioxybenzidine, 1,8-naphthalenediamine, m(p)-monomethylphenylenediamine, 3,3'-monomethylamino-4,4'-diaminobiphenyl ether, 4,N,N'-(4-aminobenzoyl)-p(m)-phenylenediamine-2,2'-bis(4-aminophenyl benzimidazol), 2,2'-bis(4-aminophenyl benzoxazol), 2,2'-bis(4-aminophenyl benzothiazole); and secondary diamines such as piperazine and piperidine and derivatives thereof; and, in particular, a nanofiltration membrane having a functional layer composed of a cross-linked polyamide containing piperazine or piperidine, expressed in terms of monomers, has a high pressure resistance and durability as well as heat resistance and chemical resistance, and is therefore preferably used. The functional layer of the nanofiltration membrane more preferably comprises a cross-linked piperazine polyamide or a cross-linked piperidine polyamide as a major component; the polyamide still more preferably comprises a cross-linked piperazine polyamide or a cross-linked piperidine polyamide as a major component and further comprises a constituting component represented by the Formula [I]; and the polyamide still more preferably comprises a cross-linked piperazine polyamide as a major component and further comprises a constituting component represented by the Formula [I]. Further, preferably, in the Formula [I], n=3. Examples of the nanofiltration membrane comprising a cross-linked piperazine polyamide as a major component and further comprises a constituting component represented by the Formula [I] include the one described in JP 62-201606 A, and particular examples of the nanofiltration membrane include a cross-linked piperazine polyamide nanofiltration membrane UTC60 manufactured by TORAY INDUSTRIES, INC.

A nanofiltration membrane is generally used as a spiral-wound membrane element, and the nanofiltration membrane used in the present invention can also be preferably used a spiral-wound membrane element. Particular examples of a preferred nanofiltration membrane which may be used include SU-210, SU-220, SU-600 and SU-610, which are nanofiltration modules manufactured by TORAY INDUSTRIES, INC, using UTC60 manufactured by the same manufacturer, which nanofiltration modules have a polyamide functional layer comprising a cross-linked piperazine polyamide as a major component and further a constituting component represented by the Formula [I]. Further particular examples of the membrane include nanofiltration membranes NF-45, NF-90, NF-200 and NF-400 manufactured by FilmTec Corporation, which have a functional layer made of a cross-linked piperazine polyamide, and nanofiltration membranes NF99, NF97 and NF99HF manufactured by Alfa-Laval, which have a polyamide functional layer.

In the present invention, the filtration of the butanol-containing solution through a nanofiltration membrane may be carried out under pressure. With a filtration pressure lower than 0.1 MPa, the membrane permeation flux decreases, and with a filtration pressure higher than 8 MPa, the membrane is damaged. Therefore, the filtration pressure is preferably within the range of 0.1 MPa to 8 MPa, and, in cases where it is within the range of 0.5 MPa to 7 MPa, the membrane permeation flux is high, so that butanol can be allowed to pass through the membrane efficiently with less possibility of causing damage to the membrane. A filtration pressure of 1 MPa to 6 MPa is especially preferred.

In the present invention, in the filtration of a butanol-containing solution through a nanofiltration membrane, the recovery of butanol can be increased by returning the retentate to the feed solution and repeating the filtration. The recovery of butanol can be calculated by measuring the total amount of butanol contained before the nanofiltration and the total amount of butanol permeated through the nanofiltration membrane, followed by calculation by Equation 1.

Recovery of butanol (%)=(total amount of butanol permeated through nanofiltration membrane/total amount of butanol contained before nanofiltration)×100 (Equation 1).

In terms of the membrane separation performance of the nanofiltration membrane used in the present invention, the membrane preferably shows a salt rejection rate of not less than 45% when an aqueous sodium chloride solution (500 mg/L) at 25° C., pH 6.5 is filtered under a filtration pressure of 0.75 MPa. Here, the salt rejection rate can be calculated by measuring the salt concentration of the permeated aqueous sodium chloride solution, followed by calculation by Equation 2.

Salt rejection rate=100×{1−(salt concentration of permeate/salt concentration of feed solution} (Equation 2).

Further, in terms of the permeation performance of the nanofiltration membrane, the membrane preferably shows a membrane permeation flux ($m^3/(m^2 \cdot day)$) of not less than 0.3 with aqueous sodium chloride solution (500 mg/L) under a filtration pressure of 0.3 MPa. The membrane permeation flux can be calculated by measuring the amount of the permeant, the length of time required for collecting this amount of the permeant, and the membrane area, followed by calculation by Equation 3.

Membrane permeation flux ($m^3/(m^2 \cdot day)$)=amount of permeant/(membrane area×collection time) (Equation 3).

In the present invention, examples of the impurities separated from the butanol-containing solution into the feed flow by the nanofiltration membrane include inorganic substances such as calcium, sodium, sulfuric acid, nitric acid and phosphoric acid; sugars such as glucose, fructose, xylose, sucrose, galactose and starch; and proteins; and mixtures thereof can also be preferably separated.

The permeability of the nanofiltration membrane to butanol in the present invention can be evaluated by calculating the permeation rate of butanol. The permeation rate of butanol can be calculated by measuring the concentration of butanol (butanol concentration of feed solution) contained in the feed solution (butanol-containing solution) and the concentration of butanol (butanol concentration of permeate) contained in the permeate (butanol solution) by analysis represented by high performance liquid chromatography and gas chromatography, followed by calculation by Equation 4.

Permeation rate of butanol (%)=(butanol concentration of permeate/butanol concentration of feed solution)×100 (Equation 4).

The permeate from the nanofiltration membrane is preferably concentrated in cases where the concentration of the substance of interest is low. In terms of the method for concentrating the permeate from the nanofiltration membrane, methods using a concentrator represented by an evaporator are commonly employed and also applicable to the present invention, but, since the heat capacity of water is much larger than those of organic solvents, enormous energy and time are required for the concentration. On the other hand, concentration by a reverse osmosis membrane is superior to concentration using an evaporator in view of reduction in the energy/cost, and therefore preferably applied to the present invention.

The reverse osmosis membrane in the present invention is a filter for removing ions and/or low molecular-weight molecules using a pressure difference larger than the osmotic pressure of the solution to be treated, and examples thereof which can be used include cellulose membranes such as those made of cellulose acetate and membranes wherein a multifunctional amine compound and a multifunctional acid halide were polycondensed to provide a separation functional layer made of a polyamide on a microporous support membrane. In order to suppress dirt, that is, fouling, on the surface of the reverse osmosis membrane, a low-fouling reverse osmosis membrane, which is mainly for sewage treatment, can also be preferably employed, which reverse osmosis membrane is prepared by covering the surface of a separation functional layer made of a polyamide with an aqueous solution of a compound having at least one reactive group reactive with an acid halide group, thereby allowing acid halide groups remaining on the surface the separation functional layer to form covalent bonds with the reactive groups. Since most of the divalent ions have been removed in the step of filtering through the nanofiltration membrane of the present invention, stable membrane concentration can be carried out without formation of scale on the surface of the reverse osmosis membrane.

Further, the term "filtering through the reverse osmosis membrane" means that the butanol-containing solution permeated through the nanofiltration membrane is concentrated by being allowed to pass through the reverse osmosis membrane, followed by collecting the resulting solution containing butanol in the concentrate flow.

Examples of the reverse osmosis membrane preferably used in the present invention include composite membranes having a cellulose acetate polymer as a functional layer (hereinafter referred to as cellulose acetate reverse osmosis membranes) and composite membranes having a polyamide functional layer (hereinafter referred to as polyamide reverse osmosis membranes). Here, examples of the cellulose acetate polymer include polymers prepared with organic acid esters of cellulose such as cellulose acetate, cellulose diacetate, cellulose triacetate, cellulose propionate and cellulose butyrate, which may be used solely, as a mixture, or as a mixed ester. Examples of the polyamide include linear polymers and cross-linked polymers constituted by aliphatic and/or aromatic diamine monomers. Examples of the form of the membrane which may be used as appropriate include the flat membrane, spiral-wound membrane and hollow fiber membrane.

Particular examples of the reverse osmosis membrane used in the present invention include polyamide reverse osmosis membrane modules manufactured by TORAY INDUSTRIES, INC., such as low-pressure type modules SU-710, SU-720, SU-720F, SU-710L, SU-720L, SU-720LF, SU-720R, SU-710P and SU-720P, as well as high-pressure type modules SU-810, SU-820, SU-820L and SU-820FA containing UTC70 as the reverse osmosis membrane; cellulose acetate reverse osmosis membranes manufactured by the same manufacturer SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D manufactured by Nitto Denko Corporation; RO98pHt, RO99, HR98PP and CE4040C-30D manufactured by Alfa-Laval; GE Sepa manufactured by GE; and BW30-4040, TW30-4040, XLE-4040, LP-4040, LE-4040, SW30-4040 and SW30HRLE-4040 manufactured by FilmTec Corporation.

In the present invention, filtration of the permeate from the nanofiltration membrane with the reverse osmosis membrane is carried out under pressure, and the filtration pressure is preferably within the range of 1 MPa to 8 MPa since, with a filtration pressure lower than 1 MPa, the membrane permeation flux decreases, and with a filtration pressure higher than 8 MPa, the membrane is damaged. Further, since, with a filtration pressure within the range of 1 MPa to 7 MPa, the membrane permeation flux is high, the butanol solution can be efficiently concentrated. The filtration pressure is most preferably within the range of 2 MPa to 6 MPa since there is less possibility of causing damage to the membrane in this case.

Further, in the present invention, by subjecting the permeate from the nanofiltration membrane to a step of distilling the permeate, highly pure butanol can be obtained. The distillation step is carried out preferably under a reduced pressure of not less than 1 Pa and not more than atmospheric pressure (normal pressure, about 101 kPa), more preferably under a reduced pressure of not less than 100 Pa and not more than 15 kPa. In cases where the distillation is carried out under reduced pressure, the distillation temperature is preferably 20° C. to 200° C., more preferably 50° C. to 150° C.

EXAMPLES

The present invention will now be described more concretely by way of Examples, but the present invention is not restricted to the Examples below.

Reference Example 1

Evaluation of Permeability of Nanofiltration Membrane to Butanol

Figure 2:
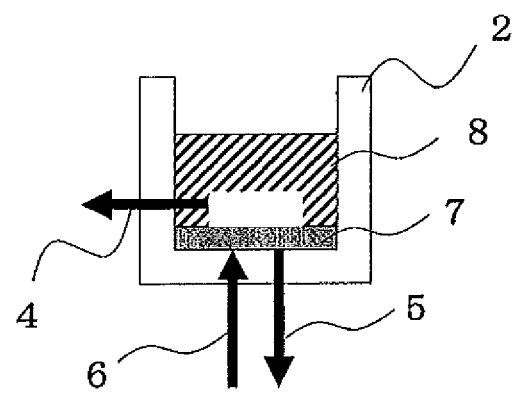
FIG. 2 is a schematic view showing an embodiment of a cross-sectional view of a cell in the separation apparatus used in the present invention having a nanofiltration membrane and a reverse osmosis membrane, which cell has the reverse osmosis membrane attached thereto.

To 20 L of ultrapure water, 20 g of n-butanol (both of which were manufactured from Wako Pure Chemical Industries, Ltd.) was added, and the resulting mixture was stirred at 25° C. for 30 minutes, thereby preparing 10 g/L butanol solution. Subsequently, 20 L of the thus prepared aqueous butanol solution was fed to a feed tank 1 of the membrane filtration apparatus shown in FIG. 1. As the 90$\phi$ nanofiltration membrane indicated by Symbol 7 in FIG. 2, each of a cross-linked piperazine polyamide nanofiltration membrane "UTC60" (nanofiltration membrane 1; manufactured by TORAY INDUSTRIES, INC.), a polyamide nanofiltration membrane "NF99" (nanofiltration membrane 2, manufactured by Alfa-Laval), a cellulose acetate nanofiltration membrane "GE Sepa" (nanofiltration membrane 3; manufactured by GE Osmonics), and a cross-linked piperazine polyamide nanofiltration membrane "NF-400" (nanofiltration membrane 4; manufactured by FilmTec Corporation) was placed in a cell made of stainless steel (SUS316), and the temperature of the feed solution was adjusted to 25° C. and the pressure of a high-pressure pump 3 was adjusted to 1 MPa, followed by collecting the permeate 4. The concentration of butanol contained in each of the feed tank 1 and the permeate 4 was analyzed with a gas chromatography: GC-2010 (manufactured by Shimadzu Corporation) under the following conditions, thereby calculating the permeation rate of butanol.

Column: TC-1, 0.53 mm I.D.×15 m, df=1.5 μm (GL Science)

Mobile phase: helium gas (7.9 mL/min., 50 to 100° C.: 5° C./min.)

Detection: FID 250° C.

The results are shown in Table 1.

TABLE 1

| | Product name (Manufacturer name) | Membrane material | Filtration pressure (MPa) | Butanol concentration in Feed (g/L) | Butanol concentration in permeate (g/L) | Permeation rate (%) |
|---|---|---|---|---|---|---|
| Nanofiltration membrane 1 | UTC60 (TORAY INDUSTRIES, INC.) | Cross-linked piperazine polyamide | 1 | 10 | 8.96 | 89.6 |
| Nanofiltration membrane 2 | NF99 (Alfa-Laval) | Polyamide | 1 | 10 | 7.47 | 74.7 |
| Nanofiltration membrane 3 | GE Sepa(GE Osmonics) | Cellulose acetate | 1 | 10 | 9.16 | 91.6 |
| Nanofiltration membrane 4 | NF-400 (FilmTec Corporation) | Cross-linked piperazine polyamide | 1 | 10 | 8.85 | 88.5 |

As shown by the results in Table 1, butanol permeated through any of the nanofiltration membranes. Further, since the permeation rates of butanol were high, a possibility that butanol can be purified from nonorganic salts and sugars at high efficiency was suggested. The differences in the permeation rate of butanol among the different types of the membrane materials were small, but the cross-linked piperazine polyamide nanofiltration membranes showed higher permeation rates of butanol, and the polyamide nanofiltration membrane showed a somewhat lower permeation rate.

Examples 1 to 9

Purification of Butanol from Fermentation Broth Using Nanofiltration Membrane

<n-Butanol Fermentation>

Two liters of the medium shown in Table 2 was prepared and adjusted to pH 6.5. The resulting medium was autoclaved (121° C., 15 minutes) and then allowed to cool to 37° C., followed by addition of 25 mL of inoculum thereto to carry out main culture. The inoculum used was prepared by culturing *Clostridium butylicum* at 37° C. for 24 hours in the same medium as that shown in Table 2 except that the glucose concentration was 50 g/L. The main culture was carried out by anaerobic culture under stirring at 100 rpm at 37° C. for 72 hours. After the culture, the bacterial cells were precipitated by centrifugation, and the culture supernatant was collected as an n-butanol-containing solution.

TABLE 2

| Medium component | Concentration [g/L] |
|---|---|
| Glucose | 150 |
| $KH_2PO_4$ | 0.8 |

TABLE 2-continued

| Medium component | Concentration [g/L] |
|---|---|
| $K_2HPO_4$ | 0.8 |
| $MgSO_4$ | 2 |
| $MnSO_4 \cdot H_2O$ | 0.01 |
| $FeSO_4 \cdot 7H_2O$ | 0.01 |
| NaCl | 1 |
| Cysteine | 0.5 |
| Asparagine | 2 |
| Yeast extract | 5 |

<Purification of n-Butanol with Nanofiltration Membrane>

Thereafter, 2 L of the culture supernatant obtained as described above was fed to the feed tank 1 of the membrane filtration apparatus shown in FIG. 1. As the 90ϕ nanofiltration membrane indicated by Symbol 7 in FIG. 2, each of the above nanofiltration membranes 1 to 3 was placed in a cell made of stainless steel (SUS316), and the pressure by the high-pressure pump 3 was adjusted to 1 MPa, 3 MPa or 5 MPa, followed by collecting the permeate 4 under the respective pressures. The concentration of n-butanol contained in each of the feed tank 1 and the permeate 4 was analyzed under the same conditions as those in Reference Example 1 using a gas chromatography (manufactured by Shimadzu Corporation). Further, the sugar concentrations (glucose, fructose and sucrose) were analyzed with a high performance liquid chromatography (manufactured by Shimadzu Corporation) under the following conditions.

Column: Luna 5u NH2 100A (manufactured by Phenomenex, Inc.), 30° C.

Mobile phase: water:acetonitrile=1:3, 0.6 mL/min.

Detector: RI.

The results are shown in Table 3.

TABLE 3

| | Nanofiltration membrane | Filtration pressure (MPa) | Flux ($m^3/m^2$/day) | Butanol Feed (g/L) | Butanol Permeate (g/L) | Butanol Permeation rate (%) | Total sugar concentration Feed (g/L) | Total sugar concentration Permeate (g/L) | Total sugar concentration Rejection rate (%) |
|---|---|---|---|---|---|---|---|---|---|
| Example 1 | Nanofiltration | 1 | 1.62 | 10 | 9.0 | 89.6 | 15 | 0.8 | 95.0 |
| Example 2 | membrane 1 | 3 | 4.83 | 10 | 8.8 | 87.7 | 15 | 0.6 | 96.0 |
| Example 3 | (UTC60) | 5 | 7.29 | 10 | 8.6 | 86.4 | 15 | 0.5 | 97.0 |
| Example 4 | Nanofiltration | 1 | 2.03 | 10 | 7.5 | 74.7 | 17 | 0.7 | 96.0 |
| Example 5 | membrane 2 | 3 | 5.83 | 10 | 6.9 | 68.8 | 17 | 0.5 | 97.0 |
| Example 6 | (NF99) | 5 | 8.54 | 10 | 6.6 | 66.1 | 17 | 0.5 | 97.0 |
| Example 7 | Nanofiltration | 1 | 2.12 | 10 | 9.2 | 91.6 | 17 | 1.2 | 93.0 |
| Example 8 | membrane 3 | 3 | 5.42 | 10 | 8.5 | 84.7 | 17 | 1.0 | 94.0 |
| Example 9 | (GE Sepa) | 5 | 8.23 | 10 | 8.4 | 83.8 | 17 | 0.8 | 95.5 |
| Example 10 | Nanofiltration | 1 | 1.55 | 10 | 8.8 | 88.2 | 17 | 0.7 | 96.0 |
| Example 11 | membrane 4 | 3 | 4.64 | 10 | 8.6 | 85.9 | 17 | 0.5 | 97.0 |
| Example 12 | (NF-400) | 5 | 7.00 | 10 | 8.5 | 84.7 | 17 | 0.5 | 97.0 |

As shown in Table 3, with all the nanofiltration membranes and under all the filtration pressures, the sugars were removed and n-butanol solutions were obtained. Further, since a colorless transparent solution was obtained from the brown-colored broth, it was assumed that the other impurities were also mostly removed. Further, when an operation in which 1.5 L of the permeate was collected and 1.5 L of distilled water was added thereto, followed by collecting the permeate again was repeated three times in order to increase the recovery of n-butanol shown by (Equation 1), the recovery became 94%.

<Distillation from Solution Concentrated Using Reverse Osmosis Membrane>

Among the n-butanol solutions obtained as described above, those of Example 2, Example 5, Example 8 and Example 11 were subjected to the study. To the feed tank 1 of the membrane filtration apparatus shown in FIG. 1, 4.5 L of the solution was fed. As the 90φ reverse osmosis membrane indicated by Symbol 7 in FIG. 2, a polyamide reverse osmosis membrane (UTC-70, manufactured by TORAY INDUSTRIES, INC.) was attached to a cell made of stainless steel (SUS316), and membrane filtration was carried out by adjusting the pressure by the high-pressure pump 3 to 5 MPa and the temperature of the feed solution to 35° C., thereby removing 4.4 L of the permeate 4 from the reverse osmosis membrane. One hundred milliliter of the thus obtained concentrate was subjected to atmospheric distillation at 117° C. The results of the distillation are shown in Table 4.

TABLE 4

| | | Butanol [g/L] | | | |
|---|---|---|---|---|---|
| | | Before concentration | After concentration | Distillation yield (%) | GC purity (%) |
| Example 2 | Nanofiltration membrane 1 | 8.8 | 396 | 95 | 99.9 |
| Example 5 | Nanofiltration membrane 2 | 6.9 | 311 | 92 | 99.8 |
| Example 8 | Nanofiltration membrane 3 | 8.5 | 383 | 90 | 99.5 |
| Example 11 | Nanofiltration membrane 4 | 8.6 | 387 | 93 | 99.9 |

From these results, it was shown that the present invention allows highly efficient production of high-purity n-butanol at low cost.

Comparative Example 1

Purification of 1,3-Propanediol with Nanofiltration Membrane

A model broth containing 1,3-propanediol was filtered through a nanofiltration membrane as follows.

In terms of the culture medium, 2.5 L of a culture medium containing 60 g/L of Yutosei (MUSO Co., Ltd.) and 1.5 g/L of ammonium sulfate was prepared and then autoclaved (121° C., 15 minutes). First, an yeast strain NBRC10505 was cultured in 5 ml of the above raw material sugar medium in a test tube overnight with shaking (pre-preculture). The pre-preculture broth was inoculated to 100 ml of a fresh lot of the above raw material sugar medium, and culture was carried out in a 500-ml Sakaguchi flask for 24 hours with shaking (preculture). The preculture broth was added to 2 L of the above raw material sugar medium, and culture was carried out while adjusting temperature and pH in a jar fermenter. The operating conditions of the jar fermenter were as shown below.

Reaction vessel volume (amount of lactic acid fermentation medium), 2 (L); temperature adjustment, 30 (° C.); ventilation volume for the reaction vessel, 0.2 (L/min.); stirring rate of the reaction vessel, 400 rpm; pH adjustment, adjusted to pH 5 with 1 N calcium hydroxide.

After 24 hours of the culture, the fermentation broth was centrifuged to remove the yeast cells, and the supernatant was collected. To this broth, 1,3-propanediol was added to 10 g/L. This broth was subjected to treatment with the nanofiltration membrane in the same manner as in the above Example 2. The resultant was further concentrated using the reverse osmosis membrane in the same manner as in the above Example 2, followed by distillation under reduced pressure (5 mmHg) at 97° C.

As a result, the distillation yield of 1,3-propanediol was 95%, and the GC purity was 99.7%. Thus, it was suggested that usage of the nanofiltration membrane allows purification of high-purity 1,3-propanediol. However, since the membrane permeability of 1,3-propanediol with respect to the nanofiltration membrane 1 (UTC60) was as low as 26%, the yield of 1,3-propanediol was lower than that of butanol. Thus, it was shown that, although 1,3-propanediol and butanol described in Example 2 have almost the same molecular weights, n-butanol shows a higher permeation rate with respect to the nanofiltration membrane, so that butanol is a compound more suitable for purification with the nanofiltration membrane.

What is claimed is:

1. A method of producing butanol, said method comprising the steps of:

filtering a butanol-containing solution through a nanofiltration membrane; and collecting butanol-containing solution from the permeate flow of said nanofiltration membrane.

2. The method according to claim 1, wherein said butanol-containing solution is a fermentation broth obtained by microbial fermentation.

3. The method according to claim 1, wherein said nanofiltration membrane has a functional layer comprising a polyamide.

4. The method according to claim 3, wherein said polyamide comprises a cross-linked piperazine polyamide as a major component, and a constituting component represented by Formula [I]:

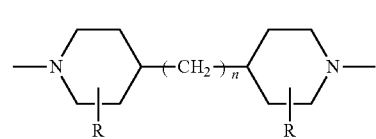

wherein R represents —H or —CH$_3$, and n represents an integer of 0 to 3.

5. The method according to claim 1, further comprising the step of filtering the collected butanol-containing solution through a reverse osmosis membrane to increase the butanol concentration.

6. The method according to claim 1, further comprising the step of distilling the collected butanol-containing solution under a pressure of not less than 1 Pa and not more than atmospheric pressure, at 25° C. to 200° C.

7. The method according to claim 5, further comprising the step of distilling the butanol-containing solution after concentration through said reverse osmosis membrane under a pressure of not less than 1 Pa and not more than atmospheric pressure, at 25° C. to 200° C.

* * * * *